United States Patent [19]

Weller, III et al.

[11] Patent Number: 5,151,513

[45] Date of Patent: Sep. 29, 1992

[54] N-HETEROCYCLIC ALCOHOL DERIVATIVES

[75] Inventors: Harold N. Weller, III, Pennington; Denis E. Ryono, Princeton, both of N.J.

[73] Assignee: E. R. Squibb & Sons, Inc., Princeton, N.J.

[21] Appl. No.: 187,782

[22] Filed: Apr. 29, 1988

[51] Int. Cl.$^5$ ............................................. C07D 413/12
[52] U.S. Cl. ................................... 544/139; 544/140; 544/141
[58] Field of Search ............................ 544/122, 235.8; 514/235.8

[56] References Cited

U.S. PATENT DOCUMENTS

| 4,638,010 | 1/1989 | Weller, III et al. | 548/336 |
| 4,656,269 | 4/1987 | Iizuka et al. | 544/139 |
| 4,665,193 | 5/1987 | Ryono et al. | 548/336 |
| 4,711,958 | 12/1987 | Iizuka et al. | 544/139 |

FOREIGN PATENT DOCUMENTS

| 5288186 | 8/1986 | Australia . |
| 0104041 | 2/1983 | European Pat. Off. . |
| 0190891 | 8/1986 | European Pat. Off. . |
| 201036 | 9/1984 | Japan . |

OTHER PUBLICATIONS

H. L. Sham, "Novel Non-Basic Bioisostere of Histidine Synthesized Form-Aspartic Acid" *J. Chem Soc. Commun.*, pp. 1792-1793 (1987).

S. Rosenberg et al., "Novel Renin inhibitors Containing Analogues of Statine Retro-Inverted at the C-Termini: specificity at the P$_2$ Histidine Site," *J. Med. Chem.*, 30, 1224-1228 (1987).

Powers et al., "Inhibition of Human Leukocyte Elastase, Porcine Pancreatic Elastase and Cathepsin G by Peptide Ketones", Proccedings from the 9th American Peptide Symposium, Jun. 23-28, 1985; Univ. of Toronto, Canada, pp. 819-822.

Plattner et al., J. Med. Chem 1988 vol. 31, pp. 2277-2288.

Burger, *Medicinal Chemistry* 2nd Ed (1960); Interscience Publishers Inc., New York, NY; pp. 565-571, 579-581, 600, & 601.

*Primary Examiner*—Robert W. Ramsuer
*Assistant Examiner*—Jacqueline Haley
*Attorney, Agent, or Firm*—Theodore R. Furman, Jr.

[57] ABSTRACT

Compounds of the formula

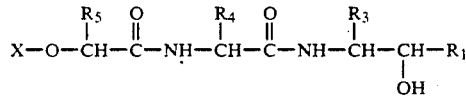

wherein R$_1$ is an N-heterocyclic group as defined herein, are disclosed. These compounds are inhibitors of renin and therefore useful as cardiovascular agents.

3 Claims, No Drawings

N-HETEROCYCLIC ALCOHOL DERIVATIVES

BACKGROUND OF THE INVENTION

Jones et al. in WO 84/03044 disclose renin inhibiting tetra-, penta-, or hexapeptide analogues of the formula $$X-D-E-A-B-Z-W$$

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbon-nitrogen link which as such or in hydrated form is an unhydrolyzable tetrahedral analogue of the transition state of the peptide bond as given above. In particular, A is defined as $$-\underset{R^5}{\overset{R_4}{\underset{|}{N}}}-\underset{R^1}{\overset{R_1}{\underset{|}{C}}}-M-\underset{R^6}{\overset{R^2}{\underset{|}{C}}}-G^1$$

wherein M can be —CH—OH.

Szelke et al. in European Patent Application 104,041 disclose renin inhibitory polypeptides including the partial sequence $$X-A-B-Z-W$$
and
$$X-Phe-His-A-B-Z-W$$

wherein A is $$-NH-\overset{R^1}{\underset{|}{CH}}-G-\overset{R^3}{\underset{|}{N}}-\overset{R^2}{\underset{|}{CH}}-\overset{O}{\underset{\|}{C}}-$$

and G is $$-\overset{OH}{\underset{|}{CH}}-CH_2,$$

X is hydrogen, protecting group, or an amino acyl residue, B is a lipophilic amino acyl residue, and Z plus W are an amino alcohol residue or Z is aminoacyl and W is hydroxy, ester, amide, etc.

Matsueda et al. in U.S. Pat. No. 4,548,926 disclose renin inhibiting peptides of the formula $$R^1-\overset{O}{\underset{\|}{C}}-NH-CH-\overset{O}{\underset{\|}{C}}-NH-\overset{But}{\underset{|}{CH}}-X$$

(with pyrrole/imidazole ring attached to CH$_2$)

wherein But represents an isobutyl or sec-butyl group and X includes a group of the formula —CH(R$^2$)—Y.

Gordon et al. in U.S. Pat. No. 4,514,391 disclose hydroxy substituted peptide compounds of the formula $$R_3-\overset{OH}{\underset{|}{CH}}-\overset{}{\underset{\underset{\underset{R_2}{|}}{\underset{C=O}{|}}}{\underset{NH}{|}}{CH}}-CH_2-\overset{R}{\underset{|}{N}}-\overset{R_1}{\underset{|}{CH}}-\overset{O}{\underset{\|}{C}}-X$$

which possess angiotensin converting enzyme or enkephalinase inhibition activity.

A copending application, U.S. Ser. No. 003,446 entitled "N-HETEROCYCLIC ALCOHOL RENIN INHIBITORS", filed Jan. 15, 1987, discloses compounds of the formula $$X-(NH-\overset{R_5}{\underset{|}{CH}}-\overset{O}{\underset{\|}{C}})_p NH-\overset{R_4}{\underset{|}{CH}}-\overset{O}{\underset{\|}{C}}-NH-\overset{R_3}{\underset{|}{CH}}-\overset{}{\underset{\underset{OH}{|}}{CH}}-R_1$$

wherein R$_1$ can be various N-heterocyclic moieties.

SUMMARY OF THE INVENTION

In accordance with the present invention novel compounds which are inhibitors of renin, and therefore useful as cardiovascular agents, are disclosed. These compounds have the formula $$X-O-\overset{R_5}{\underset{|}{CH}}-\overset{O}{\underset{\|}{C}}-NH-\overset{R_4}{\underset{|}{CH}}-\overset{O}{\underset{\|}{C}}-NH-\overset{R_3}{\underset{|}{CH}}-\overset{}{\underset{\underset{OH}{|}}{CH}}-R_1 \quad I$$

including pharmaceutically acceptable salts thereof, wherein X is $$R_6-(CH_2)_m-A-\overset{}{\underset{\underset{R_{10}}{|}}{N}}-\overset{O}{\underset{\|}{C}}-, \quad R_6-(CH_2)_m-A-\overset{O}{\underset{\|}{C}}-,$$

$$R_6-(CH_2)_m-A-O-\overset{O}{\underset{\|}{C}}-,$$

$$R_6-(CH_2)_m-A-(O)_p-\overset{O}{\underset{\|}{P}}-, \quad \overset{}{\underset{\underset{\underset{R_6'}{|}}{(CH_2)_{m'}}}{N}}-\overset{O}{\underset{\|}{C}}-, \text{ or}$$

$$R_6-(CH_2)_m-A-:$$

R$_1$ is a fully saturated, partially saturated, or unsaturated monocyclic N-heterocyclic ring of 5 or 6 atoms containing at least one N atom or a bicyclic ring in which such N-heterocyclic ring is fused to a benzene ring. The N-heterocyclic ring can also include an O or S atom or up to three additional N atoms. The N-heterocyclic ring is attached to $$-\overset{}{\underset{\underset{OH}{|}}{CH}}-$$

by way of an available carbon atom.

An available N atom in the N-heterocyclic ring can be substituted with an N-protecting group such as or 2,4-dinitrophenyl, or loweralkyl, —(CH$_2$)$_n$—[phenyl], or —(CH$_2$)$_n$-cycloalkyl.

Similarly, an available C atom in the monocyclic ring or an available C atom in the benzene portion of the bicyclic ring can be substituted with lower alkyl, —(CH$_2$)$_n$—[phenyl], or —(CH$_2$)$_n$-cycloalkyl.

Preferred N-heterocyclic rings are

[structures of preferred N-heterocyclic rings]

$R_2$ is

—CH$_2$—O—CH$_2$—[phenyl]—SO$_2$—[phenyl]—CH$_3$, 2,4-dinitrophenyl, hydrogen, lower alkyl, —(CH$_2$)$_n$—[phenyl]

or —(CH$_2$)$_n$-cycloalkyl;

N— represents a heterocyclic ring of the formula $$\begin{array}{c} (CH_2)_a \\ Y \qquad N- \\ (CH_2)_b \end{array}$$

wherein Y is —CH$_2$, O, S, or N—R$_9$, a is an integer from 1 to 4, and b is an integer from 1 to 4 provided that the sum of a plus b is an integer from 2 to 5 and such heterocyclic rings wherein one carbon atom has a lower alkyl substituent;

R$_3$ and R$_5$ are independently selected from hydrogen, lower alkyl, halo substituted lower alkyl, —(CH$_2$)$_n$—aryl, —(CH$_2$)$_n$—heterocyclo, —(CH$_2$)$_n$—OH, —(CH$_2$)$_n$—O—lower alkyl, —(CH$_2$)$_n$—NH$_2$, —(CH$_2$)$_n$—SH, —(CH$_2$)$_n$—S—lower alkyl, —(CH$_2$)$_n$—O—(CH$_2$)$_g$—OH, —(CH$_2$)$_n$—O—(CH$_2$)$_g$—NH$_2$.

—(CH$_2$)$_n$—S—(CH$_2$)$_g$—OH, —(CH$_2$)$_n$—$\overset{O}{\underset{\|}{C}}$—OH, —(CH$_2$)$_n$—S—(CH$_2$)$_g$—NH$_2$, —(CH$_2$)$_n$—NH—C$\underset{\diagdown NH_2}{\overset{\diagup NH}{}}$ , —(CH$_2$)$_n$—$\overset{O}{\underset{\|}{C}}$—NH$_2$, —(CH$_2$)$_n$—[imidazole]—N—R$_7$, —(CH$_2$)$_n$—[imidazole with R$_8$]—N, and —(CH$_2$)$_n$-cycloalkyl;

R$_4$ is selected from hydrogen, lower alkyl, halo substituted lower alkyl, —(CH$_2$)$_n$—aryl, —(CH$_2$)$_n$—heterocyclo, —(CH$_2$)$_n$—OH, —(CH$_2$)$_n$—O—lower alkyl, —(CH$_2$)$_n$—NH$_2$, —(CH$_2$)$_n$—SH, —(CH$_2$)$_n$—S—lower alkyl, —(CH$_2$)$_n$—O—(CH$_2$)$_g$—OH, —(CH$_2$)$_n$—O—(CH$_2$)$_g$—NH$_2$,

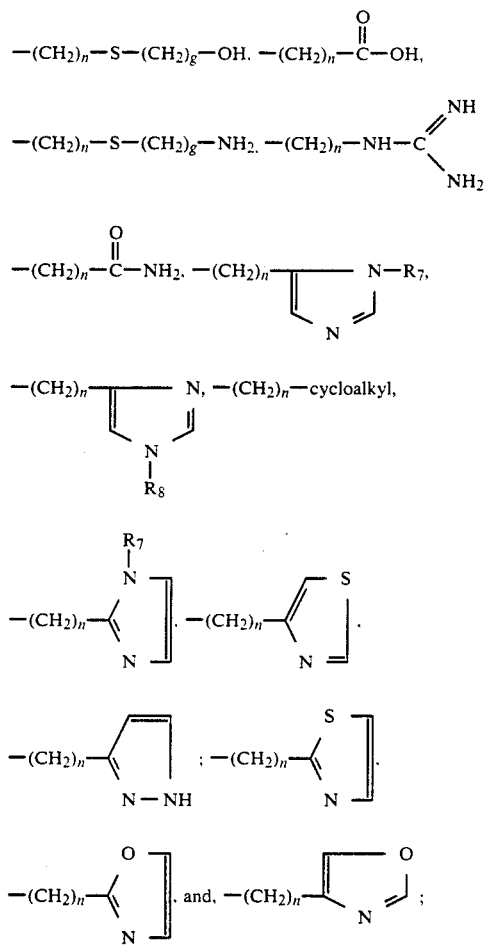

R$_6$, R$_6'$ and R$_6''$ are independently selected from hydrogen, alkyl, aryl, pyridyl and cycloalkyl, or R$_6$ and R$_6'$ taken together with the atom to which they are bonded may form a ring of 5 to 7 atoms;

m, m' and m'' are zero or an integer from 1 to 5;

n is an integer from 1 to 5;

p is zero or 1;

g is an integer from 2 to 5;

R$_7$ is

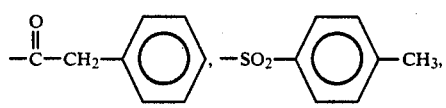

R$_8$ is 2,4-dinitrophenyl

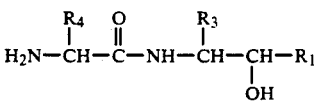

or

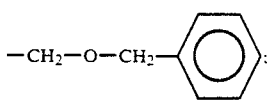

R$_9$ is hydrogen, lower alkyl, —(CH$_2$)$_n$ or —(CH$_2$)$_n$-cycloalkyl;

R$_{10}$ is —(CH$_2$)$_{m'}$—R$_6'$;

A is a single bond or —(CH)—(CH$_2$)$_{m''}$—R$_6''$.

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons. Similarly, the terms lower alkoxy and lower alkylthio refer to such lower alkyl groups attached to an oxygen or sulfur. The preferred lower alkyl groups are straight or branched chain of 1 to 5 carbons.

The term cycloalkyl refers to saturated rings of 4 to 7 carbon atoms with cyclopentyl an cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkythio of 1 to 4 carbons, lower alkoxy of 1 to 4 carbons, halogen, hydroxy, amino, -NH-alkyl wherein alkyl is of 1 to 4 carbons, or -N(alkyl)z wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two O and S atoms and/or one to four N atoms provided that the total number of hetero atoms in the ring is 4 or less further provided that if any ring includes two oxygen atoms they are separated by at least one carbon atom. The hetero ring is attached by way of an available carbon atom. Preferred hetero groups include 2-thiazolyl, 2- and 4-imidazolyl, 2- and 3-thienyl, 2- and 3-furyl, 2-, 3- and 4-pyridyl. The term hetero also includes bicyclic rings wherein the five or six membered ring containing O, S and N atoms as defined above is fused to a benzene ring. The preferred bicyclic ring is benzimidazolyl.

The compounds of formula I are prepared by coupling an amine of the formula $$\text{H}_2\text{N}-\overset{\text{R}_4}{\underset{|}{\text{CH}}}-\overset{\text{O}}{\underset{\|}{\text{C}}}-\text{NH}-\overset{\text{R}_3}{\underset{|}{\text{CH}}}-\overset{}{\underset{\underset{\text{OH}}{|}}{\text{CH}}}-\text{R}_1 \qquad \text{II}$$

with the compound of the formula

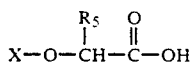 III in a solvent, e.g. dimethylformamide, and in the presence of a coupling agent, e.g. dicyclohexylcarbodiimide, and, optionally a catalyst, such as hydroxybenzotriazole hydrate.

To make the amine of formula II, a starting material, $H-R_1$, is treated with a base, such as n-butyl lithium to obtain a compound of the formula

 IV

Compound IV is thereafter reacted with an aldehyde of the formula

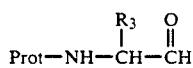 V (wherein Prot is an amino protecting group, e.g t-butoxycarbonyl) to provide the protected amine of the formula

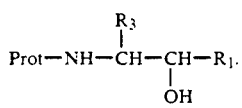 VI

Compound VI, in a solvent such as ethyl acetate, can be deprotected by means known in the art, e.g. by treatment with hydrogen chloride, to provide an amine of the formula

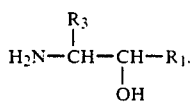 VII

The amine of formula II can then be prepared by reacting the deprotected amine of formula VII with an N-protected amino acid of the formula

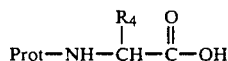 VIII in the presence of a coupling agent, such as dicyclohexylcarbodiimide, and thereafter removing the protecting group by known means, e.g. treatment with hydrogen chloride in the case of a t-butoxycarbonyl protecting group.

To make the compounds of formula I wherein X is

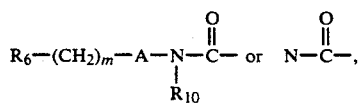

a compound of the formula

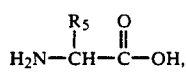 IX in sulfuric acid, is treated with sodium nitrite in water to provide a compound having the formula

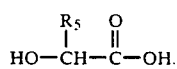 X

Compound X, in an organic solvent, such as dimethylformamide, and in the presence of a base, such as sodium bicarbonate, is treated with benzyl bromide to provide a compound of the formula

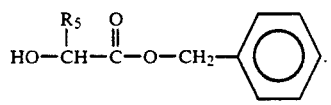 XI

Compound XI, in N-methyl morpholine and methylene chloride, is thereafter reacted with p-nitrophenyl choroformate,

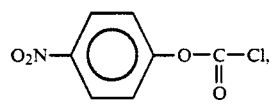 XII in a solvent, such as methylene chloride, to yield a compound of the formula

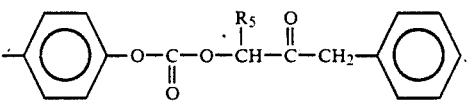 XIII

Compound XIII, in a solvent, such as toluene, can be reacted with a compound of the formula $R_6-(CH_2)_m-A-N-H$  XIVa
           |
          $R_{10}$ or N—H  XIVb to provide an intermediate of the formula

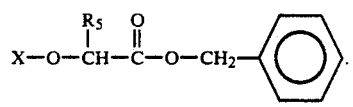

Reduction of compound XV, for example by hydrogenation in ethyl acetate in the presence of a palladium/carbon catalyst, provides the compounds of formula III. Reaction with an amine of formula II (or a protected form thereof), as described above, provides the compounds of formula I wherein X is

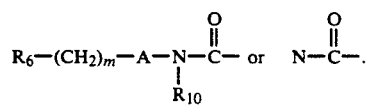

To prepare the compounds of formula I wherein X is

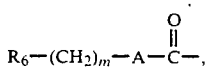

an intermediate of formula XI in a solvent, such as methylene chloride, is reacted with a carboxylic acid of the formula

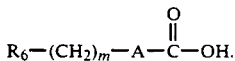     XVI

This is carried out in the presence of dimethylaminopyridine and dicyclohexylcarbodiimide and provides a compound of formula XV where X is

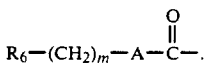

This so-formed intermediate is treated with a base, such as sodium hydroxide, to provide a corresponding compound of formula III and reacted with the amine of formula II, as above, to provide the compounds of formula I wherein X is

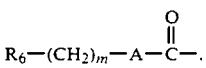

To prepare the compounds of formula I wherein X is

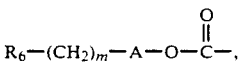

a compound of the formula

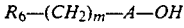     XVII in a solvent, such as methylene chloride, is reacted with an excess of phosgene to give a compound of the formula

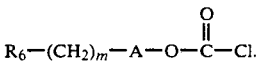     XVIII

A compound of formula XVIII in a solvent, such as methylene chloride, is reacted with an intermediate of formula XI, preferably in the presence of a base, e.g. triethylamine. The product can be reduced and coupled with an intermediate of formula II, as above, to provide the corresponding compounds of formula I where X is

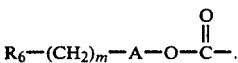

To prepare the compounds of formula I wherein X is $R_6-(CH_2)_m-A-$, a compound of the formula

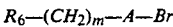     XIX is reacted with the compound of formula XI in a solvent, such as tetrahydrofuran, and in the presence of a base, such as sodium hydroxide, to give

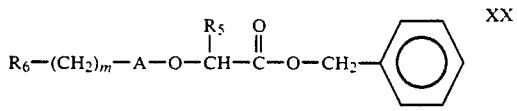     XX which can be reduced to give

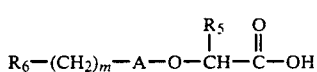     XXI which can be coupled with II to give I.

To prepare the compounds of formula I wherein X is

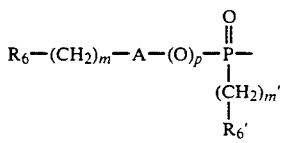

and p is zero, a compound of the formula $R_6'-(CH_2)_{m'}-Br$     XXII is reacted with dimethylchlorophosphite to provide compound of the formula

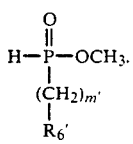     XXIII

Compound XXIII is reacted with a compound of the formula $R_6-(CH_2)_m-A-MgBr$     XXIV in a solvent, such as tetrahydrofuran, to provide

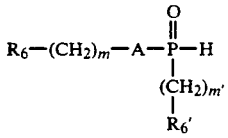     XXV which can be treated with phosphorous pentachloride to provide a compound of the formula

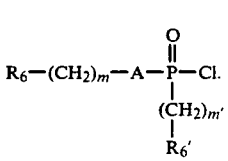     XXVI

Compound XXVI is reacted with compound XI in a solvent, such as dichloromethane, and in the presence of triethylamine to provide

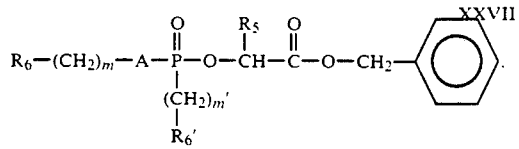
XXVII

Compound XXVII is reduced or saponified to the corresponding carboxylic acid III which is reacted with the amine II as above to provide compounds of formula I where X is

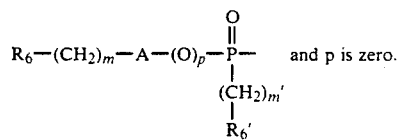

and p is zero.

To prepare the compounds of formula I wherein X is 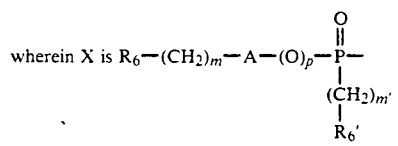

methanol is reacted with phosphorous trichloride in the presence of a base, such as triethylamine, and the resulting product is treated with aqueous sodium hydroxide to give a compound of the formula

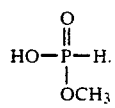 XXVIII

Reaction of compound XXVIII with a compound of the formula

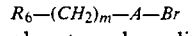 XXIX in a solvent, such as dichloromethane, and in the presence of triethylamine and dimethylamine pyridine provides a compound of the formula

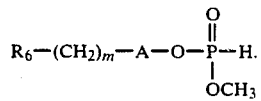 XXX

Compound XXX is reacted with a compound of the formula

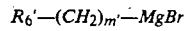 XXXI in a solvent, such as tetrahydrofuran, to give

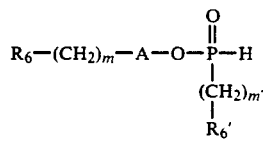 XXXII which can be treated with thionyl chloride to provide a compound of the formula

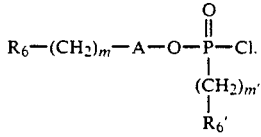 XXXIII

Reaction of compound XXXIII with XI in a solvent, such as dichloromethane, and in the presence of triethylamine and dimethylamino pyridine provides the ester

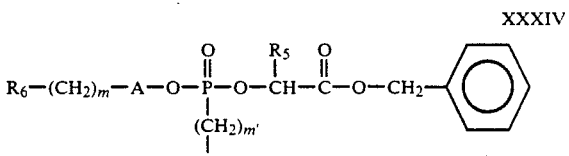 XXXIV which can be reduced or saponified to the corresponding carboxylic acid III which is reacted with amine II as above to provide compounds of formula I where X is

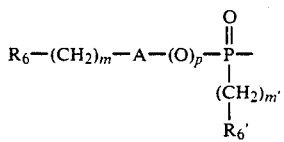

and
p is one.

In the above reactions, if any of $R_3$, $R_4$ and $R_5$ are —$(CH_2)_n$-aryl wherein aryl is phenyl, 1-naphthyl, 2-naphthyl substituted with one or more hydroxy or amino groups, —$(CH_2)_n$-heterocyclo wherein heterocyclo is an imidazolyl, —$(CH_2)_n$—SH, —$(CH_2)_n$—OH,

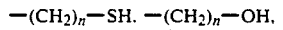
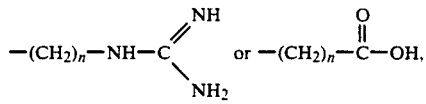

then the hydroxyl, amino, imidazolyl, mercaptan, carboxyl, or guanidinyl function should be protected during the reaction. Suitable protecting groups include benzyloxycarbonyl, t-butoxycarbonyl, benzyl, benzhydryl, trityl, tosyl, etc., and nitro in the case of guanidinyl. The protecting group is removed by hydrogenation, treatment with acid, or by other known means following completion of the reaction.

The various peptide intermediates employed in above procedures are known in the literature or can be readily prepared by known methods. See for example, the Peptides, Volume 1, "Major Methods of Peptide Bond Formation", Academic Press (1979).

Preferred compounds of this invention are those of formula I wherein X is

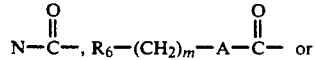

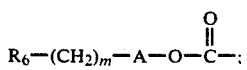

$R_1$ is

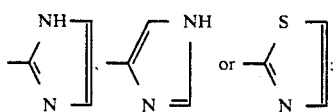

$R_3$ is straight or branched chain lower alkyl of 3 to 5 carbons, —$(CH_2)_n$-cyclopentyl, —$(CH_2)_n$-cyclohexyl, or

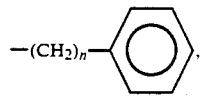

wherein n is an integer from 1 to 3;

$R_4$ is hydrogen, straight or branched chain lower alkyl of up to 5 carbons, —$(CH_2)_4$—$NH_2$,

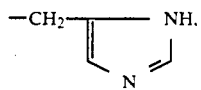

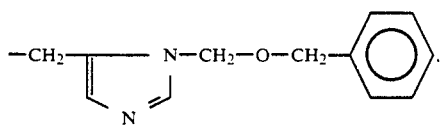

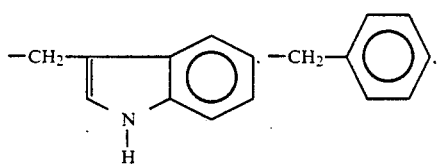

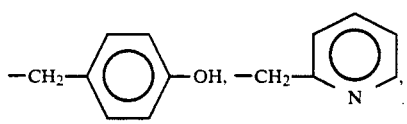

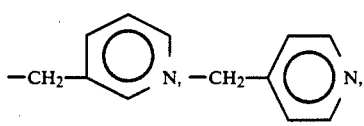

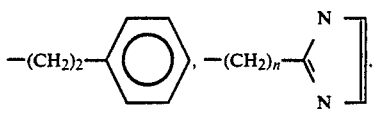

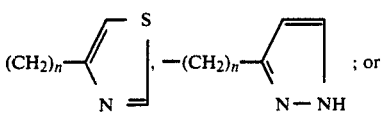

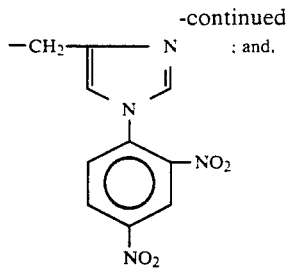

$R_5$ is straight or branched chain lower alkyl of up to 5 carbons,

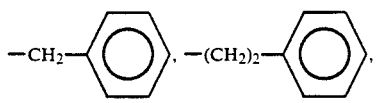

—$CH_2$—($\alpha$-naphthyl), —$CH_2$—($\beta$-naphthyl),

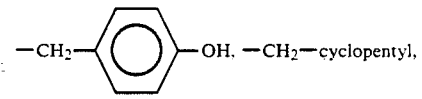

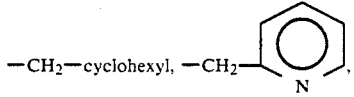

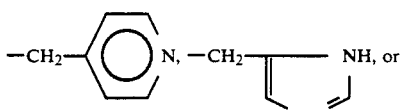

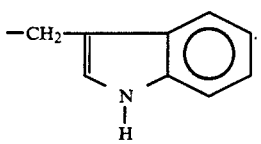

Most preferred are those compounds of formula I wherein $R_6$ is cycloalkyl, morpholinyl, ethyl or ethoxy;

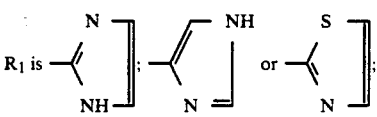

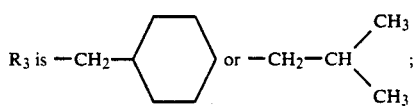

-continued

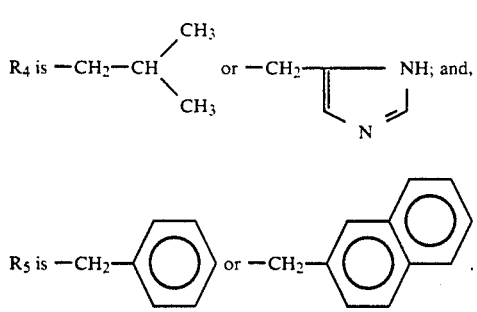

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of $R_3$, $R_4$ and $R_5$ are other than hydrogen and at the carbon to which the —OH group is attached. Thus, the compounds of formula I can exist in diastereoisomeric forms or in mixtures thereof. The above-described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg, preferably about 250 to 500 mg per kg of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg, preferably about 3000 to 4000 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will now be described by the following examples, however, the invention should not be limited to the details therein

EXAMPLE 1

[(S)-2-[(4-Morpholinylcarbonyl)oxy]-1-oxo-3-phenylpropyl]-N-[(1S,2R)-1-(cyclohexylmethyl)-2-hydroxy-2-(1H-imidazol-2-yl)ethyl]-L-histidinamide, dihydrochloride A. (S)-α-Hydroxybenzenepropanoic acid A solution of sodium nitrite (51.8 g, 720 mmol) in 200 mL of water was added dropwise over 6 hours to a stirred solution of L-phenylalanine (33.04 g, 200 mmol) in 500 mL of 10% sulfuric acid at 50° C. After the addition was complete, the reaction mixture was stirred for 3 hours at 50° C, then at room temperature overnight. The reaction mixture was extracted with ethyl acetate (3×200 mL, 2×100 mL), then the combined organic extract was washed with water and brine, dried over sodium sulfate and evaporated to yield 28.98 g of a yellow solid. Recrystallization from benzene afforded 22.15 g of the title A compound as white needles, m.p. 120°-124° C.

B. (S)-α-Hydroxybenzenepropanoic acid, phenylmethyl ester

To mixture of the title A compound (9.97 g, 60 mmols) and sodium bicarbonate (10 g, 120 mmols) in dimethyformamide (50 mL) was added a solution of benzyl bromide (7.13 mL, 60 mmols) in dimethylformamide (10 mL). The mixture was stirred at 25° C. under argon for 48 hours, after which it was concentrated in vacuo. The residue was dissolved in ethyl acetate and washed with water, saturated sodium bicarbonate solution, and brine, dried over anhydrous magnesium sulfate, and concentrated. The residue (12.7 g) was chromatographed on silica gel (eluting with 4:1 hexane:ethyl acetate) to give 12 g of the title B compound.

C.
(S)-α-[[(4-Nitrophenoxy)carbonyl]oxy]benzene-propanoic acid, phenylmethyl ester To a solution of the title B compound (1.28 g, 5.0 mmols) and N-methyl morpholine (0.6 mL, 5.5 mmols) in methylene chloride (20 mL) at −30° C. was added a solution of 4-nitrophenyl chloroformate (1.1 g, 5.5 mmol) in methylene chloride (5 mL). The mixture was stirred at 25° C. for 15 minutes, after which it was washed sequentially with 1N hydrochloric acid and saturated sodium bicarbonate solution, dried over anhydrous magnesium sulfate, and concentrated in vacuo. The residue (2.04 g) was chromatographed on silica gel (eluting with benzene) to give 1.7 g of the title C compound as a colorless oil.

D.
(S)-α-[(4-Morpholinylcarbonyl)oxy]benzenepropanoic acid, phenylmethyl ester To a solution of the title C compound (1.52 g, 3.6 mmols) in toluene (12 mL) at 25° C. was added morpholine (0.4 mL, 4.5 mmol). The resulting mixture was stirred for 18 hours at 25° C., after which it was concentrated in vacuo. The residue was dissolved in ethyl acetate and the solution was washed with saturated potassium carbonate solution until the washes were colorless. The organic extract was dried over anhydrous magnesium sulfate and concentrated in vacuo. The residue (1.3 g) was chromatographed on silica gel (eluting with 2:1 hexane:ethyl acetate) to give 1.1 of the title D compound.

E.
(S)-α-[(4-Morpholinylcarbonyl)oxy]benzenepropanoic acid

A mixture of the title D compound (1 g, 2.7 mmols) and 20% palladium hydroxide on carbon (200 mg) in ethyl acetate (20 mL) was hydrogenated for 1 hour at one atmosphere and 25° C., after which it was filtered and concentrated in vacuo to give 850 mg of the title E compound.

F.
(S)-2-[[(1,1-Dimethylethoxy)carbonyl]amino]-2-phenyl-methyl-1-ethanol To a solution containing N-[(1,1-dimethylethoxy)carbonyl]-L-phenylalanine (10 g, 37.7 mmole) in dimethylformamide (40 ml) is added solid sodium bicarbonate (4.75 g, 56.6 mmole) and iodomethane (16 g, 113 mmole). The mixture is heated at 40° under argon for 12 hours, the cooled and the reaction mixture partitioned between water (150 ml) and ether (250 ml). The organic layer is rinsed with 2% aqueous sodium bicarbonate (2×100 ml), 2% aqueous sodium bisulfite (100 ml), water (2 ×100 ml), and brine, dried over magnesium sulfate, and concentrated in vacuo to give 10.5 g of N-[(1,1-dimethylethoxy)carbonyl]-L-phenylalanine, methyl ester as an oil.

To a solution containing N-[(1,1-dimethyl-ethoxy)-carbonyl]-L-phenylalanine, methyl ester (10 g, 35.8 mmole) dissolved in a mixture of tetrahydrofuran (190 ml) and absolute ethanol (190 ml) is added lithium chloride (6.09 g, 143.2 mmole). The resulting homogeneous solution is treated with sodium borohydride (5.42 g, 143.2 mmole) and the reaction is stirred at room temperature under argon for 24 hours. The reaction mixture is next filtered using ether (~700 ml) to rinse the filter cake. The resulting filtrate is rinsed with water (3×200 ml) and brine (200 ml), dried over magnesium sulfate, and concentrated in vacuo to give 9 g of crude product. Recrystal-lization from ether/hexane gives 7.59 g of the title F compound; m.p. 94°-96°.

Analysis calc'd for $C_{14}H_{21}NIO_3$:
C, 66.90; H, 8.42; N, 5.57;
Found: C, 66.80; H, 8.57; N, 5.38.

G.
[(S)-2-Cyclohexyl-1-(hydroxymethyl)ethyl]carbamic acid, 1,1-dimethylethyl ester A solution of the title F compound (7 g, 27.8 mmole) in methanol (70 ml) is hydrogenated at 55 psi on a Parr Shaker using 5% rhodium on alumina (500 mg) as catalyst. After 17 hours, the reaction mixture is filtered and concentrated in vacuo to yield 7.36 g of the title G compound as an oil.

Analysis calc'd for $C_{14}H_{27}NO_3$:
C, 65.33; H, 10.57; N, 5.44
Found: C, 64.94; H, 10.55; N, 5.23.

H. (S)-(2-Cyclohexyl-1-formylethyl)carbamic acid, 1,1-dimethylethyl ester

A solution of the title G compound (4.6 g, 17.9 mmole) in methylene chloride (40 ml) is added to a mixture of Dess-Martin periodinane reagent (8 g, 19 mmole) [prepared according to Dess et al., J. Org. Chem., Vol. 48, p. 4155 (1983)]and t-butanol (1.5 g, 19 mmole) in methylene chloride (70 ml) which had been stirred at room temperature before the addition. A slight exotherm (to 32° ) results. After 30 minutes, the reaction mixture is quenched in ether (800 ml), resulting in the separation of a white solid. A mixture of sodium thiosulfate pentahydrate (31.3 g, 126 mmole) in saturated sodium bicarbonate solution (200 ml) is added, with stirring. The resulting two-phase mixture is separated and the organic phase is washed with water, saturated sodium bicarbonate (2×100 ml), water, and brine, dried over magnesium sulfate, and concentrated in vacuo to give 3.8 g of the title H compound as a colorless oil.

I.
[(1S)-1-(Cyclohexylmethyl)-2-hydroxy-2-[1-[(phenylmethoxy)methyl]-1H-imidazol-2-yl]ethyl]carbamic acid, 1,1-dimethylethyl ester 2.5 M n-Butyllithium solution in hexane (12 ml, 31 mmole) is added to a solution of 1-[(phenylmethoxy)methyl]-1H-imidazole (5.3 g, 28 mmole) in tetrahydrofuran (90 ml) at −70° under argon. After stirring for 15 minutes, the title H compound (3.6 g, 14 mmole) in tetrahydrofuran (36 ml) is added dropwise over a period of 5 minutes at a reaction temperature of −65° to −70°. After 2 hours at −70°, the bath is warmed to 0° and saturated ammonium chloride (25 ml) is added followed by ether (300 ml) and water (2×50 ml) and brine, dried over magnesium sulfate, and concentrated in vacuo. The resulting crude product (8.4 g) is flash chromatographed eluting with acetone:petroleum ether (1:4) to give 580 mg of a fast moving isomer, 370 mg of a mixed fraction and 2 g of the title I compound (slow moving isomer).

J.
[R-(R*,S*)]-α-(1-Amino-2-cyclohexylethyl)-1-[(phenylmethoxy)methyl]-1H-imidazole-2-methanol A solution of the title I compound (3.92 g, 8.83 mmols) in ethyl acetate (200 mL) was cooled to 0° C. and hydrochloric acid gas was bubbled through the solution for 30 minutes. The mixture was then stirred for 3.5 hours as it warmed to room temperature, after which it was concentrated in vacuo to give the title J compound as a white power (3.56 g 97%).

K. L-Histidine, methyl ester, dihydrochloride

To a stirred solution (ice-bath) of L-histidine (38.75 g, 240 mmol) in methanol (500 ml), thionyl chloride (27.2 ml, 375 mmol) was added in drops. After fifteen minutes the ice bath was removed and the reaction mixture was stirred at room temperature for one hour. Then after refluxing for 48 hours, it was concentrated in vacuo. The separated crystals were filtered using methanol for washing (48.93 g). The methanolic solution on dilution with ether afforded additional 10 g of the title K compound, m.p. 208°–209°.

L. N,1-Bis[(1,1-dimethylethoxy)carbonyl]-L-histidine, methyl ester

To a suspension of the title K compound (24.2 g, 100 mmol) in methanol (80 ml) were added triethyl amine (28 ml, 200 mmol) and di-tert-butyl dicarbonate (48 g, 220 mmol). After 3.5 hours, it was filtered and the methanolic solution concentrated in vacuo. The residue was taken into chloroform and washed with 10% citric acid. The crude product on crystallization from isopropyl ether afforded 23.1 g of the title L compound, m.p. 88°–95° C. After evaporation and redissolution of the mother liquor (15.75 g) in methanol (50 ml) di-tert-butyl dicarbonate (10 g, 45.9 mmol) was added. After stirring the reaction mixture overnight it was evaporated, taken into chloroform and washed with 10% citric acid. The residue after chromatography over silica gel yielded 6.4 g of homogeneous title L compound.

M.
N-[(1,1-Dimethylethoxy)carbonyl]-3-[(phenylmethoxy)methyl]-L-histidine, methyl ester, monohydrochloride To a solution of the title L compound (24.7 g, 66.9 mmol) in dry methylene chloride (156 ml), benzylchloromethyl ether (11.6 ml, 88.6 mmol) was added and the reaction mixture stirred at room temperature for 5 hours. After concentration in vacuo and on dissolution in ethyl acetate (100 ml), the title M compound crystallized out (17.85 g, 65%), m.p. 152°–153° C.

N.
N-[(1,1-Dimethylethoxy)carbonyl]-3-[(phenylmethoxy)methyl]-L-histidine

The title M compound (18.66 g, 43.8 mmol) was dissolved in methanol (50 ml). Aqueous sodium hydroxide (1N, 92 ml) was added followed by water 83 ml). After keeping the reaction mixture at room temperature for 90 minutes it was further diluted by the addition of water (650 ml) and acidified to pH 4.5 using aqueous hydrochloric acid. The aqueous solution was extracted with chloroform. The chloroform solution was evaporated and the residue was crystallized from ethyl acetate (15.13 g, 92%), m.p. 155°–157° C.

O.
[(1,1-Dimethylethoxy)carbonyl]-N-[(1S,2R)-1-(cyclohexylmethyl)-2-hydroxy-2-[1-[(phenylmethoxy)methyl]-1H-imidazol-2-yl]ethyl]-3-[(phenylmethoxy)methyl]-L-histidinamide To a solution of the title J compound (3.06 g, 7.35 mmols), 1-hydroxybenzotriazole hydrate (1.13 g, 7.35 mmols), and the title N compound (2.76 g, 7.35 mmols) in tetrahydrofuran (20 mL) were added triethylamine (2.06 mL, 14.7 mmol) and dicyclohexylcarbodiimide (1.52 g, 7.35 mmol). The mixture was stirred for 18 hours at 25° C., after which it was filtered. The filtrate was diluted with ethyl acetate, washed with saturated sodium bicarbonate solution, dried over anhydrous magnesium sulfate and concentrated The residue (4.92 g) was chromatographed on Merck silica gel, eluting with ethyl acetate:pyridine:acetic acid:water (80:20:6:11) to give the title 0 compound as the major product (3.98 g, 77%).

P.
N-[(1S,2R)-1-(Cyclohexylmethyl)-2-hydroxy-2-[1-[(phenylmethoxy)methyl]-(1H-imidazol-2-yl]-ethyl]-3-[(phenylmethoxy)methyl]-L-histidinamide A solution of the title 0 compound (3.88 g, 5.53 mmol) in ethyl acetate (200 mL) was cooled to 0° C. in an ice bath and hydrochloric acid gas was bubbled through the solution for 30 minutes. The resulting mixture was then stirred for 2.5 hours as it warmed to 25° C., after which it was concentrated to small volume. The resulting white precipitate was collected on a PTFE filter to give the title P compound as a white powder (3.33 g, 85%), m.p. 143°–157° C.

[(S)-2-[(4-Morpholinylcarbonyl)oxy]-1-oxo-3-phenylpropyl]-N-[(1S,2R)-1-(cyclohexylcarbonyl)-2-hydroxy-2-1-[(phenylmethoxy) methyl]-1H-imidazol-2-yl]ethyl]-3-[(phenylmethoxy)-methyl-L-histidinamide To a mixture of the title P compound (1.49 g, 2.0 mmols), the title E compound (670 mg, 2.2 mmols) and 1-hydroxybenzotriazole hydrate (337 mg, 2.20 mmols) in tetrahydrofuran (8 mL) at 0° C. were added triethylamine (0.84 mL, 6.0 mmols) and dicyclohexylcarbodiimide (453 mg, 2.20 mmols) The resulting mixture was stirred for 18 hours as it warmed to 25° C., after which it was filtered. The filtrate was diluted with ethyl acetate, washed with saturated sodium bicarbonate solution and brine, dried over anhydrous magnesium sulfate, and concentrated The residue (1.68 g) was flash chromatographed on silica gel, eluting with ethyl acetate:-pyridine:acetic acid:water (100:20:6:11), to give 1.44 g of the title Q compound as the major product.

R.
[(S)-2-[(4-Morpholinylcarbonyl)oxy]-1-oxo-3-phenylpropyl]-N-[(1S,2R)-1-(cyclohexylmethyl)-2-hydroxy-2-(1H-imidazol-2-yl)ethyl]-L-histidinamide, dihydrochloride A mixture of the title Q compound (1.4 g, 1.6 mmols), 1N hydrochloric acid (3.5 mL, 3.5 mmol) and 20% palladium hydroxide on carbon (300 mg) in methanol (20 mL) was stirred under a stream of hydrogen for 18 hours, after which it was filtered (PTFE filter) and concentrated. The residue was dissolved in water, treated with activated charcoal, filtered and the solution was lyophilized to give 812 mg of the title compound as an off white solid.

Microanalysis calc'd for C$_{32}$H$_{43}$N$_7$O$_6$·2.25HCL·4-H$_2$O:
C, 49.54; H, 6.92; N, 12.64; Cl, 10.28;
Found: C, 49.43; H, 6.96; N, 12.38; Cl, 10.33.

EXAMPLE 2

[(S)-2-[(Cyclopentylcarbonyl)oxy]-1-oxo-3-phenyl-propyl]-N-[(1S,2R)-1-(cyclohexylmethyl)-2-hydroxy-2-(1H-imidazol-2-yl)ethyl]-L-histidinamide, dihydrochloride A. (S)-α-[(Cyclopentylcarbonyl)oxy]benzenepropanoic acid, phenylmethyl ester To a solution of the title B compound of Example 1 (2.56 g, 10 mmol), cyclopentane carboxylic acid (1.1 mL, 10 mmol), and dimethylaminopyridine (122 mg, 1.0 mmol) methylene chloride (40 mL) at 0° C. was added dicyclohexylcarbodiimide (2.06 g, 10 mmol). The resulting mixture was stirred at 25° C. for 18 hours, after which it was filtered. The filtrate was washed with saturated aqueous sodium bicarbonate solution and brine, dried over anhydrous magnesium sulfate, and concentrated in vacuo. The residue (3.5 g) was purified by flash chromatography on silica gel, eluting with toluene:ethyl acetate (6:1) to give 3.27 g of the title A compound as a colorless oil.

B. (S)-α-[(Cyclopentylcarbonyl)oxy]benzenepropanoic acid

A mixture of the title A compound (3.15 g, 8.94 mmol) and 20% palladium hydroxide on carbon (1 g) in ethyl acetate (40 mL) was hydrogenated under a slow stream of hydrogen for 1.5 hours, after which it was filtered The filtrate was concentrated and the residue crystallized from hexane to give 1 7 g of the title B compound, m.p 69°–71° C.

C.

[(S)-2-[(Cyclopentylcarbonyl)oxy]-1-oxo-3-phenyl-propyl]-N-[(1S,2R)-1-(cyclohexylcarbonyl)-2-hydroxy-2-[1-[(phenylmethoxy)methyl]-1H-imidazol-2-yl]ethyl]-3-[(phenylmethoxy)methyl]-L-histidinamide To a solution of the title P compound of Example 1 (1.12 g, 1.50 mmol), 1-hydroxybenzo-triazole hydrate (252 mg, 1.65 mmol), and the title B compound (493 mg, 1.65 mmol) in dimethyl-formamide (7.5 mL) were added triethylamine (0.63 mL, 4.5 mmol) and dicyclohexylcarbodiimide (340 mg, 1.65 mmol). The mixture was stirred for 18 hours at 25° C., after which it was filtered. The filtrate was dissolved in ethyl acetate, washed with saturated sodium bicarbonate solution, dried over anhydrous magnesium sulfate, and concentrated. The residue was purified by flash chromatography on silica gel, eluting with ethyl acetate:buffer 5:1 (pyridine: acetic acid:water, 20:6:11), to give 1.14 g of the title C compound as a colorless oil.

D.

[(S)-2-[(Cyclopentylcarbonyl)oxy]-1-oxo-3-phenyl-propyl]-N-[(1S,2R)-1-(cyclohexylmethyl)-2-hydroxy-2-(1H-imidazol-2-yl)ethyl]-L-histidinamide, dihydrochloride A mixture of the title C compound (1.04 g, 1.23 mmol), 1N hydrochloric acid (2.46 mL, 2.46 mmol) and 20% palladium hydroxide on carbon (500 mg) in dioxane (18 mL) and water (2 mL) was hydrogenated under a slow stream of hydrogen for seven days. The mixture was filtered and concentrated and the residue was purified by flash chromatography on silica gel, eluting with ethyl acetate:buffer 2:1 (pyridine:acetic acid:water, 20:6:11). The major product was dissolved in excess 1N hydrochloric acid and concentrated in vacuo. The residue was lyophilized from water to give the title compound as a fluffy white powder.

Microanalysis cal'd for C$_{33}$H$_{44}$N$_6$O$_5$·2.2HCl·H$_2$O:
C, 56.38; H, 6 91; N, 11 95; Cl, 11.10;
Found: C, 56.29; H, 6.80; N, 11.89; Cl, 11.14.

EXAMPLE 3

N-[(1S,2R)-1-(Cyclohexylmethyl)-2-hydroxy-2-(1H-imidazol-2-yl)ethyl]-N2-(S)-2-hydroxy1-oxo-3-phenyl-propyl)-L-histidinamide, 2.7 hydrochloride

A.

[(S)-2-Hydroxy-1-oxo-3-phenylpropyl]-N-[(1S,-2R)-1-(cyclohexylmethyl)-2-hydroxy-2-1-[(phenylmethoxy)methyl]-1H-imidazol-2-yl]-ethyl]-3-[(phenylmethoxy)methyl]-L-histidinamide To a solution of the title P compound of Example 1 (746 mg, 1.0 mmol), 1-hydroxybenzo-triazole hydrate (168 mg, 1.1 mmol) and the title A compound of Example 1 (183 mg, 1.1 mmol) in tetrahydrofuran (5 mL) at 0° C. were added triethyl-amine (0.42 mL, 3.0 mmols) and dicyclohexylcarbodiimide (227 mg, 1.1 mmol). The resulting mixture was stirred for 18 hours at 25° C., after which it was filtered. The filtrate was diluted with ethyl acetate, washed with saturated sodium bicarbonate solution and brine, dried over anhydrous magnesium sulfate and concentrated The residue was chromatographed on silica gel, eluting with ethyl acetate pyridine:acetic acid:water (100:20:6:11) to give the title A compound as the major product (670 mg), $[\alpha]_D = -27.3°$ (c=0.75, CH$_3$OH).

B.

N-[(1S,2R)-1-(Cyclohexylmethyl)-2-hydroxy-2-(1H-imidazol-2-yl)ethyl]-N2-[(S)-2-hydroxy-1-oxo-3-phenylpropyl]-L-histidinamide, 2.7 hydrochloride A mixture of the title A compound (600 mg, 0.8 mmol), 20% palladium hydroxide on carbon (150 mg) and 1.0N hydrochloric acid (1.8 mL, 1.8 mmols) in methanol (20 mL) was hydrogenated under a slow stream of hydrogen for 20 hours The mixture was then filtered and concentrated to dryness. The residue (470 mg) was dissolved in water and lyophilized to give the title compound as a white solid (437 mg).

EXAMPLES 4–15

Following the procedures of Examples 1, 2 and 3 and as outlined above, additional compounds within the scope of this invention can be prepared having the formula $$X-O-\underset{R_5}{\underset{|}{CH}}-\underset{O}{\underset{\|}{C}}-NH-\underset{R_4}{\underset{|}{CH}}-\underset{O}{\underset{\|}{C}}-NH-\underset{R_3}{\underset{|}{CH}}-\underset{OH}{\underset{|}{CH}}-R_1$$

wherein the substituents are as defined below.

| Ex. No. | X | $R_5$ | $R_4$ | $R_3$ | $R_1$ |
|---|---|---|---|---|---|
| 4 | morpholine-N-C(=O)- | -CH$_2$-phenyl | -CH$_2$-(imidazol-4-yl, NH) | -CH$_2$-cyclohexyl | imidazol-2-yl (NH) |
| 5 | " | " | -CH$_2$-CH(CH$_3$)$_2$ | " | imidazol-2-yl (NH) |
| 6 | 4-methylpiperazine-1-C(=O)- | " | -CH$_2$-(imidazol-4-yl, NH) | " | " |
| 7 | morpholine-N-C(=O)- | " | " | " | thiazol-2-yl |
| 8 | cyclohexyl-P(=O)(OCH$_2$CH$_3$)- | -CH$_2$-naphthyl | -CH$_2$-(imidazol-4-yl, NH) | -CH$_2$-cyclohexyl | imidazol-2-yl (NH) |
| 9 | cyclohexyl-O-C(=O)- | -CH$_2$-phenyl | " | " | " |
| 10 | (CH$_3$)$_2$CH-C(=O)- | -CH$_2$-naphthyl | " | " | imidazol-2-yl (NH) |
| 11 | cyclohexyl-CH$_2$-CH$_2$- | -CH$_2$-phenyl | -CH$_2$-CH(CH$_3$)$_2$ | " | imidazol-2-yl (NH) |
| 12 | (CH$_3$CH$_2$)$_2$N-C(=O)- | -CH$_2$-phenyl | -CH$_2$-(imidazol-4-yl, NH) | -CH$_2$-cyclohexyl | imidazol-2-yl (NH) |
| 13 | CH$_3$CH$_2$-P(=O)(CH$_2$CH$_3$)- | " | " | " | " |
| 14 | morpholine-N-C(=O)- | " | -CH$_2$-CH(CH$_3$)$_2$ | " | thiazol-2-yl |

-continued

| Ex. No. | X | R$_5$ | R$_4$ | R$_3$ | R$_1$ |
|---|---|---|---|---|---|
| 15 | CH$_2$CH$_3$—O—P(=O)(CH$_2$CH$_3$)— | " | " | " | (imidazol-2-yl group) |

What is claimed is:

1. A compound of the formula (morpholine-N—C(=O)—O—CH(R$_5$)—C(=O)—NH—)

—CH(R$_4$)—C(=O)—NH—CH(R$_3$)—CH(OH)—R$_1$ wherein

R$_1$ is (pyrazole/imidazole structures with R$_7$, R$_9$)

R$_3$ is hydrogen, lower alkyl, halo substituted lower alkyl or —(CH$_2$)$_n$-cycloalkyl;

R$_4$ is hydrogen, lower alkyl, halo substituted lower alkyl,

—(CH$_2$)$_n$—(imidazolyl with R$_7$) or —(CH$_2$)$_n$—(pyrazolyl);

R$_5$ is hydrogen, lower alkyl, halo-substituted lower alkyl or —(CH$_2$)$_n$-aryl;

R$_7$ is hydrogen, alkyl,

—CH$_2$—O—CH$_2$—phenyl or

—CH$_2$—phenyl;

R$_9$ is hydrogen, lower alkyl or —(CH$_2$)$_n$cycloalkyl; and n=1–3.

2. A compound of claim 1 wherein

R$_1$ is (imidazol-2-yl structure with NH)

R$_3$ is

—CH$_2$—cyclohexyl;

R$_4$ is

—CH$_2$—(imidazolyl with NH);

R$_5$ is

—CH$_2$—phenyl.

3. A compound of claim 1 having the name [(S)-2-[(4-morpholinylcarbonyl)oxy[-1-oxo-3-phenylpropyl]-N-(1S,2R)-1-(cyclohexylmethyl)-2-hydroxy-2-(1H-imidazol-2-yl)ethyl]-L-histidinamide, dihydrochloride.

* * * * *